June 27, 1961 W. E. LAMMERTS Plant Pat. 2,066
ROSE PLANT
Filed Sept. 19, 1960
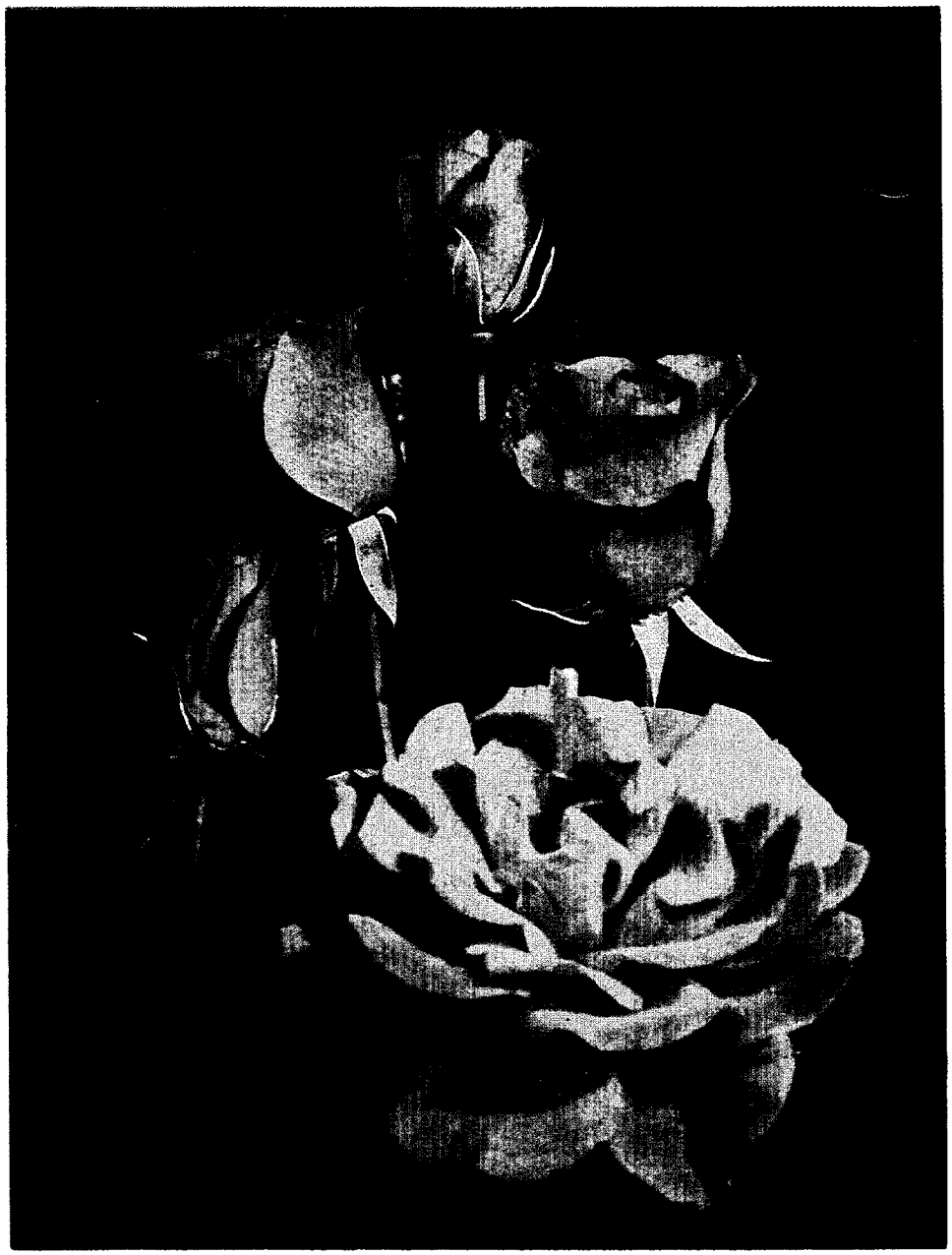
INVENTOR
Walter E. Lammerts
BY Robb & Robb
ATTORNEYS United States Patent Office Plant Pat. 2,066
Patented June 27, 1961

2,066
ROSE PLANT

Walter E. Lammerts, Livermore, Calif., assignor to Germain's, Inc., Los Angeles, Calif., a corporation of California Filed Sept. 19, 1960, Ser. No. 57,087
1 Claim. (Cl. 47—61)

The present invention relates to a new and distinct variety of rose plant of the hybrid tea class, which was originated by me by crossing the variety "Charlotte Armstrong" (Plant Patent No. 455) with an unnamed and unpatented first generation hybrid of "Charlotte Armstrong" × "Floradora" (unpatented).

The unnamed hybrid parent above referred to was the pollen parent of the new variety and was a sister seedling of the variety "Queen Elizabeth" (Pl. Pat. No. 1,259) which also originated as a cross of "Charlotte Armstrong" × "Floradora." It had a bud color corresponding to Indian Lake, Plate 826 (Horticultural Colour Chart of the British Colour Council) before the calyx breaks and Indian Lake, Plate 826/2 after the calyx breaks. This color lightens to Chrysanthemum Crimson, Plate 824/1 both inside and out as the first petal opens, while the general color effect of the open flower was from Rose Red, Plate 724 to Tyrian Purple, Plate 727, with the outside petal surface more Rose Red, Plate 724 than the present new variety. The flower of the unnamed pollen parent was about the same size as that of the new variety, but had fewer petals (only from 10 to 15 petals plus 3 or 4 petaloids), and because of this, the flower was from cup-shaped to flat. Also, the bud form as the flower opened was often poor because of so few petals, and was not high-centered. While the bush of the pollen parent of the new variety was very vigorous and bore large glossy foliage that was resistant to mildew and rust, the low flower petalage was very unsatisfactory and I therefore crossed it back with "Charlotte Armstrong" in the hope of improving the bud and flower form by increasing the petalage, while preserving the glossy foilage and vivid color. This objective was successfully achieved in the new variety which is the subject hereof.

As the result of this breeding, I have produced a new rose variety which is distinctly different from both parents, as well as from all other varieties of its class of which I am aware, and which is endowed with commercially desirable features representing a unique combination of characteristics, as evidenced by the following characteristics which are outstanding in the new variety:

(1) A tall, vigorous, grandiflora habit of growth;
(2) Large, glossy foliage, having high resistance to mildew and rust;
(3) Abundant flower production;
(4) Long-pointed buds which have a graceful urn-shaped appearance as they open;
(5) A distinctive dark maroon-red general color tonality of the buds;
(6) A distinctive and predominantly Rose Red general color tonality of the open flowers; and
(7) A luminescent quality of the flowers, accompanied by good color retention and a very slow fading habit.

In comparison with the parent variety "Charlotte Armstrong," my new variety has foliage that is more glossy, its flower buds are much darker in color, and its habit is more compact and upright. The buds of the new variety are smaller, shorter and open to smaller sized flowers than those of "Charlotte Armstrong," the buds of which are a much lighter Cherry Red color than the Maroon Red color of the buds of my new variety. From the parent variety "Charlotte Armstrong," the new variety inherits a tendency of the flower petals to remain upright and cover the stamens and pistils, while the new variety inherits the luminescent quality of the flowers from its floribunda grandparent "Floradora" and, accordingly, the open flowers of the new variety are a very bright Rose Red color and they fade very slowly.

The buds of my new variety are generally similar in color to those of the variety "Merry Widow" (Plant Patent No. 1,711), but the plants of my new variety have more attractive, super-glossy, Dark Green foliage, and the plants are more branching at the base than those of the variety "Merry Widow," which has a more compact habit of growth. The new growth of "Merry Widow" has only semi-glossy leaves which become glossy as they mature.

The new variety also resembles the variety "Carrousel" (Plant Patent No. 1,066) in respect to the color of the flowers. Both are grandifloras and about equally vigorous and similar in habit of growth. However, the buds of "Carrousel" are short-ovoid and do not develop the long urn-shaped form that is typical of the buds of my new variety. In the case of the cluster flowers of "Carrousel," they are borne on shorter stems and therefore are not as useful for cut flowers as those of my new variety, and the flowers of "Carrousel" tend to "blue" more rapidly than those of my new variety which have a luminescent quality similar to the variety "Starfire" (Plant Patent No. 1,742).

On the other hand, the new variety is readily distinguished from the variety "Starfire" by the much darker Maroon Red color in the buds and by the predominantly Rose Red color in the open flowers, as compared with the Currant Red color of "Starfire." Also, the habit of "Starfire" is more bushy and lower growing.

Another variety with which my new variety may be favorably compared is "El Capitan" (Plant Patent No. 1,796), but the flowers of the latter have a lighter Red color both in the bud and open flower stages. Also, the buds of "El Capitan" are shorter.

Asexual reproduction of my new variety by budding, as performed by me at Livermore, California, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with the Horticultural Colour Chart of the British Colour Council, except where general color terms of ordinary dictionary significance are obvious, as based upon observations of specimens grown at Livermore, California:

Type: Half-hardy; bush; seedling; for garden decoration.
Class: Hybrid tea.
Breeding: Seedling.
*Seed parent.*—"Charlotte Armstrong."
*Pollen parent.*—An unnamed $F_1$ hybrid of "Charlotte, Armstrong" × "Floradora."
Propagation: Holds its distinguishing characteristics through succeeding propagations by budding.

*Flower*

Flowers borne: Singly and several to stem; in regular rounded clusters; on strong stems of medium length.
Quantity of bloom: Abundant, outdoors.
Continuity: Continuous.
Fragrance: Moderate.
*Nature.*—Sweet Tea Rose.

Bud:

*Peduncle.*—Long; from slender to medium caliper; erect; almost smooth; with numerous red hairs. Color—Reddish Green.

*Before calyx breaks.*—Size—medium large. Form—long; pointed; without foliaceous appendages on the surface of the bud, and without slender foliaceous parts on the end of the sepals extending beyond the tip of the bud. Color—Maroon, Plate 1030.

*As calyx breaks.*—Color—from Maroon, Plate 1030 to Maroon, Plate 1030/2.

*As first petal opens.*—Size—medium. Form—from long-pointed to urn-shaped. Color—outside: Very uniform Chrysanthemum Crimson, Plate 824/1; inside—from Chrysanthemum Crimson, Plate 824/1 to Maroom, Plate 1030/1.

*Opening.*—Opens best in hot weather ranging from 80° to 90° F., and is essentially a "hot weather" rose; is retarded from opening by cold, wet weather.

Bloom:

*Size (when fully open).*—Large; from 4 inches to 5 inches.

*Petalage.*—Double; from 20 petals, plus from 3 to 6 petaloids, to 25 petals, plus from 1 to 3 petaloids; arranged regularly.

*Form.*—Very high-centered at first, but becoming open; petals being at first loosely rolled outward, but later becoming flat at maturity.

Petals:

*Texture.*—Medium thick; soft. Inside—velvety. Outside—from dull to slightly shiny.

*Shape.*—Outside—obovate, with apex usually entire or with one or two small notches. Intermediate—obovate, with apex usually entire and rarely notched. Inside—obovate, with apex usually entire and very rarely notched.

This description of a newly opened flower was made from a rose grown outdoors in the month of June at Livermore, California:

*Color.*—*Outer petal*—outside surface: Tyrian Purple, Plate 727; inside surface: From Rose Red, Plate 724 to Tyrian Purple, Plate 727, with small areas of Chrysanthemum Crimson, Plate 824/1 near edges. *Intermediate petal*—outside surface: Tyrian Purple, Plate 727; inside surface: from Rose Red, Plate 724 to Tyrian Purple, Plate 727. *Inner petal*—outside surface: Tyrian Purple, Plate 727; inside surface: from Rose Red, Plate 724 to Tyrian Purple, Plate 727.

This description was made from a rose that was open for three days outdoors in the month of June at Livermore, California:

*Color.*—*Outer petal*—outside surface: Solferino Purple, Plate 26/1; inside surface: Spiraea Red, Plate 025 at base, shading to Rose Red, Plate 724 tinged with Tyrian Purple, Plate 727 above. Inner petal—outside surface: Solferino Purple, Plate 26/1; inside surface: Spiraea Red, Plate 025 at base, shading to Rose Red, Plate 724 tinged with Tyrian Purple, Plate 727 above.

*General color effect.*—*Newly opened flower*—from Rose Red, Plate 724 to Tyrian Purple, Plate 727. 3-days open—from Spiraea Red, Plate 025 to Rose Red, Plate 724 tinged with Tyrian Purple, Plate 727.

*Behavior.*—Drop off cleanly; good color retention and slow fading; slower opening during cold, wet weather, with resulting greater emphasis of Tyrian Purple color than in normal warm weather when the color is predominently Rose Red even after 3 days, but retains a clear Rose Red color longer than many other Red roses.

*Flower longevity.*—On bush in garden—3days in June. Cut roses grown outdoors and kept at living-room temperatures—3 days in June.

*Reproductive organs*

Stamens: Many; regularly arranged about pistils.

Filaments: From short to medium length.

*Color.*—China Rose, Plate 024/1.

Anthers: Medium size.

*Color.*—Indian Yellow, Plate 6/3.

Pollen: Moderate quantity.

*Color.*—Yellow.

Pistils: Many.

Styles: Uneven; medium length; medium heavy; loosely bunched.

*Color.*—From Aureolin, Plate 3/3 at base to China Rose, Plate 024/1.

Stigma: *Color.*—Aureolin, Plate 3/3.

Ovaries: All enclosed in calyx.

Hips: Pear-shaped; smooth; thin walls.

*Color.*—Yellow.

Sepals: Permanent; spear-shaped; recurved.

*Color.*—Lavender Green, Plate 000761/1 tinged with Anthocyanin (reddish) pigment.

Seeds: Many; medium large.

*Plant*

Foliage:

*Leaves.*—Compound of 5 to 7 leaflets; very abundant; large; glossy.

*Leaflets.*—*Shape*—oval, with apex acute. Base—round. Margin—simply serrate.

*Color.*—*Mature*—Upper surface: Spinach Green, Plate 0960. Under surface: Spinach Green, Plate 0960/3. *Young*—Upper surface: Green-Bronze, but basically Spinach Green, Plate 0960/2; as leaf matures, Bronze color decreases and upper surface of leaf darkens to Spinach Green, Plate 0960. Under surface: more Bronze overtones than upper surface, but becomes lighter with maturity and basically Spinach Green, Plate 0960/3.

*Rachis (the supporting stem of the compound leaf).*—Medium heavy. Upper side—smooth; grooved. Under side—sparsely prickly.

*Stipules.*—Medium length; narrow; with medium long points turning out at an angle of 45°.

*Disease resistance.*—Highly resistant to rust and mildew, as compared with other varieties grown under comparable cultural conditions at Livermore, California.

Growth:

*Habit.*—Upright; tall; compact; generally a gradiflora habit with flowers occurring abundantly both singly on long cutting stems and in clusters.

*Growth.*—Free; vigorous.

*Canes.*—Medium heavy.

*Main stems.*—*Color*—Lettuce Green, Plate 861. *Thorns*—many; medium length; straight; with long, narrow base. *Prickles*—few; color: Green-Bronze. *Hairs*—none.

*Branches.*—*Color*—Lettuce Green, Plate 861 tinged with Bronze. *Thorns*—many; medium length; hooked downward; with long, narrow base. *Prickles*—many; color: Reddish Green. *Hairs*—few; color: Reddish Green.

*New shoots.*—*Color*—Lettuce Green, Plate 861, heavily tinged with Bronze. *Thorns*—many; medium length; hooked downward; with long, narrow base. *Prickles*—many; color: Reddish Green. *Hairs*—few; color: Reddish Green.

I claim:

A new and distinct variety of rose plant of the hybrid tea class, substantially as herein shown and described, characterized particularly as to novelty by the unique combination of a tall, vigorous, grandiflora habit of growth, large, glossy foliage having high resistance to mildew and rust, abundant flower production, long-pointed buds which have a graceful urn-shaped appearance as they open, a distinctive dark Maroon-Red general color tonality of the buds, a distinctive and predominantly Rose Red general color tonality of the open flowers, and a luminescent quality of the flowers accompanied by good color retention and a very slow fading habit.

No references cited.